(12) United States Patent
Carr et al.

(10) Patent No.: US 6,228,353 B1
(45) Date of Patent: *May 8, 2001

(54) HAIR TREATMENT COMPOSITION

(75) Inventors: Stuart William Carr, New South Wales (AU); Melvin Carvell, Bebington; Paul Alfred Cornwell, St. Albans, both of (GB); Therese Desmond, Ballina (IE); Andrew Mark Waller, Little Stanney (GB); Johann Wilhelm Wiechers, Gouda (NL)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,025

(22) Filed: Mar. 5, 1999

Related U.S. Application Data

(62) Division of application No. 08/959,863, filed on Oct. 29, 1997, now Pat. No. 5,911,978.

(30) Foreign Application Priority Data

Oct. 31, 1996 (GB) .................................................. 9622659

(51) Int. Cl.[7] .................................................. A61K 7/09

(52) U.S. Cl. ..................... 424/70.51; 424/401; 424/70.1; 424/70.11

(58) Field of Search ................................... 424/401, 70.1, 424/70.11, 70.51

(56) References Cited

U.S. PATENT DOCUMENTS

| | | | |
|---|---|---|---|
| 4,009,256 | 2/1977 | Nowak, Jr. et al. | 424/70 |
| 4,173,453 | * 11/1979 | Shiah | 8/10.1 |
| 4,652,445 | * 3/1987 | Ort | 424/70 |
| 4,837,012 | * 6/1989 | Kiffel | 424/70 |
| 5,256,407 | * 10/1993 | Gough | 424/71 |
| 5,470,876 | * 11/1995 | Proctor | 514/492 |
| 5,911,978 | * 6/1999 | Carr et al. | 424/70.1 |

FOREIGN PATENT DOCUMENTS

| | | |
|---|---|---|
| 405097645 | * 4/1993 | (JP) . |
| 92/10178 | 6/1992 | (WO) . |
| 94/03156 | 2/1994 | (WO) . |

* cited by examiner

*Primary Examiner*—Thurman K. Page
*Assistant Examiner*—Lakshmi Channavajjala
(74) *Attorney, Agent, or Firm*—Matthew Boxer

(57) ABSTRACT

A rinse-off hair treatment composition for improved delivery of amino-acid to the hair and/or scalp comprising:
(a) a particulate metal-amino acid complex;
(b) at least one surfactant; and
(c) a deposition aid.

12 Claims, 1 Drawing Sheet

HAIR TREATMENT COMPOSITION

This application is a division of Ser. No. 08/959,863 filed Oct. 29, 1997, now U.S. Pat. No. 5,911,978.

FIELD OF THE INVENTION

This invention relates to hair treatment compositions, and more particularly to hair treatment compositions formulated to be rinsed from the scalp after application and which contain amino acid actives to modify or nourish the hair or hair root.

BACKGROUND AND PRIOR ART

Amino acids are known to be important for the nourishment of the human hair root and the growth of human hair. For example, keratin hydrolysates, a source of amino acids in both free and peptide form, are a common ingredient of hair shampoos and the like. Numerous publications describe the use of an array of amino acids in lotions or tonics for topical application to cure baldness and other skin, scalp and hair disorders.

However, to achieve efficacy from rinse-off hair treatment formulations it is necessary to deliver active ingredients to the site of action, and the benefits attainable are frequently limited for substances such as amino acids, since a large proportion tends to be removed during the rinse stage.

Conventional approaches to this problem have entailed increasing application time, and increasing concentration of the active ingredient in the formulation. For example, Franz et al, Fundam.Appl.Toxicol. 21 (1993) 213–221 demonstrates different rank orders for penetration from various generic prototype personal products formulations as a function of the applied dose. This is not feasible under normal in-use conditions, and can result in barrier damage through prolonged contact time.

There is therefore a need for a rinse-off hair treatment proving enhanced delivery of amino acid.

Metal-amino acid complexes are known and available as such from the prior art. There is a body of literature describing the complexes as a way to administer metals as dietary supplements in a non-toxic way to animals. The amino acid is there to reduce the toxicology profile of heavy metals. In the personal care area, metal-amino acid complexes have been used in hair colouring compositions (Cu or Zn cysteinate, U.S. Pat. No. 4 173,453), antipruritic drugs (zinc-aminoacid conjugates, WO92/10178), and anti-inflammatory creams (SU 1382477). However improved deposition/substantivity of the amino acid portion in a topical formulation is not discussed. GB 937,362 describes compositions for the care and growth of skin, hair and nails containing one or more magnesium compounds of an alpha-aminoacid. The acid residue is described as a carrier for the specific introduction of magnesium into the skin and hair cells. U.S. Pat. No. 4,652,445 describes a no-rinse hair conditioner product with the addition of "zinc-releasing ingredients" to supplement the hair fibre with zinc. The zinc-releasing chemicals may be zinc amino acid complexes, but are preferably zinc-protein or zinc-keratin.

It has now been found that enhanced deposition of amino acid from a rinse-off hair treatment composition can be achieved by incorporation of the amino acid into the composition as a complex with a metal ion. This offers a performance and cost advantage through improved delivery of the amino acid nutrient to the target substrate, ie hair and/or scalp, per unit dose.

SUMMARY OF THE INVENTION

In one aspect the present invention provides a rinse-off hair treatment composition for improved delivery of amino-acid to the hair and/or scalp comprising:

(a) a particulate metal-amino acid complex;

(b) at least one surfactant; and (c) a deposition aid.

In a second aspect the invention provides a method of enhancing the deposition-of an amino acid from a rinse-off hair treatment composition, comprising incorporating the amino acid into the composition in the form of a particulate metal-amino acid complex.

In a third aspect the invention provides the use of a particulate metal-amino acid complex, for enhancing the deposition of amino acid from a rinse-off hair treatment composition.

DETAILED DESCRIPTION AND PREFERRED EMBODIMENTS

Amino Acid

Examples of the amino acid moiety from which the particulate metal-amino acid complex is derived include:

arginine aspartic acid citrulline cysteine cystine cystathionine glutamic acid glutamine glycine isoleucine lysine methionine ornithine serine, and valine.

Particularly preferred are cysteine, arginine, serine, glutamic acid, glutamine, isoleucine, lysine, methionine and valine.

It is also possible to employ derivatives of the amino acids. Examples include where free -NH2 groups of the amino acid are modified by one or more of the following:

(i) acyl groups, eg N-alkanoyl in which the alkanoyl moiety has an alkyl chain length of from 3 to 20 carbon atoms, preferably from 4 to 10, eg N-butanoyl, N-hexanoyl, and N-octanoyl;

(ii) ester groups, eg those in which the alkyl group is straight chain and of from 1 to 20 carbon atoms, preferably from 1 to 4 carbon atoms, eg methyl, ethyl and n-propyl;

(iii) amino acid residues; and (iv) peptide residues comprising from 2 to 8 amino acid residues.

Mixtures of the amino acids or derivatives thereof may also be used. A single molecule of metal complex itself may also contain different amino acids.

Metal Ion

Preferably the metal ion has a valency of at least 2.

Examples of the metal ion from which the particulate metal-amino acid complex is derived include Fe, Cu, Ca, Mn, Sn, Ti and Zn. The most preferred metal ion is Zn; this is thought to confer damage protection to the hair.

Mixtures of metal ions may be used. Also, the same molecule of metal complex may contain more than one metal ion, which metal ions may be the same or different.

In highly preferred compositions of the present invention, the particulate metal-amino acid complex is zinc cysteinate or zinc glutamate, or a mixture of the two.

Particle Size

The average particle size of the metal-amino acid complex in compositions of the invention may range from 0.05 to 50 microns. Our studies,(using fluorescent microspheres of different sizes as model particles, with visualisation of particle deposition on the skin using confocal laser scanning microscopy) indicate that particle size does influence the extent and location of deposition, and that a particularly preferred average particle size range for targeted delivery to the hair follicles is 3–10 microns.

The amount of particulate metal-amino acid complex incorporated in compositions of the invention is suitably from bout 0.001 to about 10% by weight of the total composition, ore preferably from about 0.1 to about 5% by weight.

Surfactant

The composition according to the invention comprises at least one surfactant, preferably chosen from anionic, cationic, nonionic, amphoteric and zwitterionic surfactants, and mixtures thereof.

A particularly preferred hair treatment composition in accordance with the invention is a shampoo composition in which at least one surfactant provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, amnonium lauryl sulphate and ammonium lauryl ether sulphate 1EO, 2EO and 3EO.

Nonionic surfactants suitable for use in compositions of the invention may include condensation products of aliphatic (C8–C18) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamnhopropionate.

The surfactants are present in shampoo compositions of the invention in an amount of from 0.1 to 50% by weight, preferably from 0.5 to 30% by weight.

Hair treatment compositions in accordance with the invention may also take the form of hair conditioning compositions, which preferably comprise one or more cationic surfactants. The use of cationic surfactants is especially preferred, because these ingredients are capable of providing conditioning benefits to hair.

Examples of cationic surfactants include:

quaternary armnonium hydroxides, e.g., tetramethylanmonium hydroxide, alkyltrimethylammonium hydroxides wherein the alkyl group has from about 8 to 22 carbon atoms, for example octyltrimethylammonium hydroxide, dodecyltrimethy- ammonium hydroxide, hexadecyltrimethylammonium hydroxide, cetyltrimethylammonium hydroxide, octyldimethylbenzylammonium hydroxide, decyldimethyl- benzylanmonium hydroxide, stearyldimethylbenzylammonium hydroxide, didodecyldimethylarmonium hydroxide, dioctadecyldimethylaimmonium hydroxide, tallow trimethylanmonium hydroxide, cocotrimethylannonium hydroxide, and the corresponding salts thereof, e.g., chlorides Cetylpyridinium hydroxide or salts thereof, e.g., chloride Quaternium -5

Quaternium -31

Quaternium -18 and mixtures thereof.

In hair conditioning compositions according to the invention, the level of cationic surfactant is preferably from 0.01 to 10%, more preferably 0.05 to 5%, most preferably 0.1 to 2% by weight of the composition.

Deposition Aid

In accordance with the invention, the hair treatment composition contains a polymeric water-soluble deposition aid for the particles of metal-amino acid complex. By "deposition aid" is meant an agent which enhances deposition of the particles of metal-amino acid complex on the intended site, i.e., the hair and/or the scalp.

The deposition aid will generally be present at levels of from 0.01 to 5%, preferably from about 0.05 to 1%, more preferably from about 0.08% to about 0.5% by weight. The deposition aid may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic charge density of the deposition aid, which is defined as the reciprocal of the molecular weight of a monomeric unit of the polymer containing 1 charge, has been found to need to be at least 0.1 meq/g, preferably above 0.8 or higher. The cationic charge density should not exceed 4 meq/g, it is preferably less than 3 and more preferably less than 2 meq/g. The charge density can be measured using conductimetric analysis and should be within the above limits at the desired pH of use, which will in general be from about 3 to 9 and preferably between 4 and 8.

The cationic nitrogen-containing group will generally be present as a substituent on a fraction of the total monomer units of the deposition aid. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic -cationic nitrogen-containing rings such as pyridinium, imidazolium, and quaternized pyrrolidine, e.g., alkyl vinyl imidazolium, alkyl vinyl pyridinium, and alkyl vinyl pyrrolidine salts. The alkyl portions of these ,monomers are preferably lower alkyls such as the C1–C3 alkyls, more preferably C1 and C2 alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1–C7 hydrocarbyls, more preferably C1–C3, alkyls.

The deposition aid can comprise mixtures of monomer units derived from amine- and/or quaternary ammonium-substituted monomer and/or compatible spacer monomers.

Suitable deposition aids include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16); copolymers of 1-vinyl-2-30 pyrrolidine and dimethylaminoethyl methacrylate (referred to in the industry by CTFA as Polyquaternium-11; cationic diallyl quaternary ammonium-containing polymers including, for example, dimethyldiallylammonium chloride homopolymer (referred to in the industry (CTFA) as Polyquaternium 6); ineral acid salts of amino-alkyl esters of homo-and copolymers of unsaturated carboxylic acids having from 3 to 5 carbon atoms, as described in U.S. Pat. No. 4,009,256; and cationic polyacrylamides as described in UK Application No. 9403156.4.

Other cationic deposition aids that can be used include cationic guar gum derivatives, such as guar hydroxypropyltrimonium chloride (Commercially available from Celanese Corp. in their Jaguar trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the deposition aid is selected from the group comprising cationic polyacrylamides, and cationic guar derivatives. Particularly preferred deposition aids are Jaguar C13S with a cationic charge density of 0.8 meq/g. Other particularly suitable materials include Jaguar C15, Jaguar C17 and Jaguar C16 and Jaguar C162.

Suspending Agent

The composition may optionally further comprise from 0.1 to 5 % of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan Chemical Co. under the trademark Stepan TAB-2)

Suitable cross linked polymers of acrylic acid and acrylate esters are Pemulen TR1 or Pemulen TR2. A suitable heteropolysaccharide gum is xanthan gum, for example that available as Kelzan mu.

Conditioning Agents

Hair treatment compositions of the invention may also optionally contain one or more conditioning agents, as are well known in the art. The conditioning agents may include silicones, protein hydrolysates, quaternised protein hydrolysates, and other materials which are known in the art as having. desirable hair conditioning properties.

Silicones are the most preferred conditioning agents.

Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition.

Advantageously, a silicone with a viscosity in the range 1–20 million cst is used. The silicone is preferably emulsion-polymerised, since this enables silicones of very high viscosity to be more easily processed. The silicone can be cross-linked.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

Fatty Alcohol

Another ingredient that may optionally be incorporated into hair treatment compositions of the invention is a fatty alcohol material. The use of these materials is especially advantageous in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

Water

The hair treatment compositions of the invention are preferably aqueous based. The compositions suitably comprise water in amount of from about 20 to about 99% by weight of the total composition.

Method of Use

The compositions of the invention are preferably rinse-off compositions, i.e., suitable for applying to the hair and/or scalp, left thereon for an appropriate period of time and then rinsed off with water. Thus, shampoos are a particularly preferred product form for compositions of the invention.

Other Optional Ingredients

Depending on the type of composition employed, one or more additional ingredients conventionally incorporated into hair treatment formulations may be included in the compositions of the invention. Such additional ingredients include opacifiers such as polyethylene glycol distearate and ethylene glycol stearates, polymer lattices, additional anti-microbial agents, foam boosters, perfumes, colouring agents, preservatives, viscosity modifiers, proteins, polymers, buffering or pH adjusting agents, moisturising agents, herb or other plant extracts and other natural ingredients.

BRIEF DESCRIPTION OF DRAWINGS

The invention is further illustrated by way of the following non-limitative examples, in which.

EXAMPLES

Materials

Figure 1:
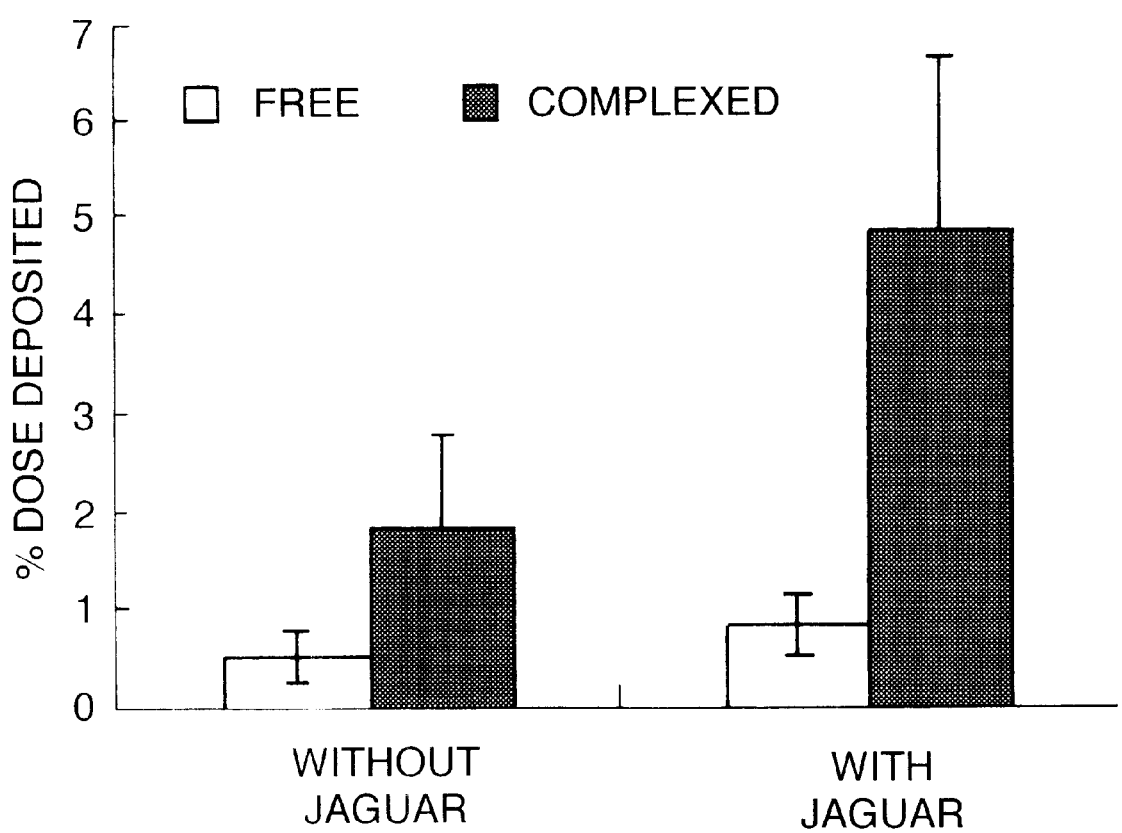
FIG. 1 is a graph showing the % dose deposition onto dermatomed pig skin in vitro of cysteine in both free and metal complexed form from a shampoo base.

Radiolabelled and non-radiolabelled cysteine for the synthesis of zinc cysteinate was obtained as follows: L-[$^{35}$S]-cysteine (>1000 Ci/mmol) in a stabilising solution containing potassium acetate, 20 mM, and dithiothreitol, 5 mM, at pH7 was purchased from Amersham International Plc (Little Chalfont, U.K.). L-Cysteine (approx. 98%) was obtained from Sigma Chemical Co. (St Louis, M.o., U.S.A.).

Dulbecco's phosphate buffered saline (10× concentrate) and penicillin/streptomycin (5000 IU/ml/5000 g/ml) were purchased from Life technologies Ltd (Paisley, U.K.). Anhydrous D-(+)-glucose was obtained from Sherman Chemicals Ltd (Sandy, U.K.). Buffer was prepared with distilled water.

Methods

1. Synthesis of Zinc Cysteinate

Basic zinc carbonate (10 g) was added to a solution of cysteine in water (14.92 g/100 ml) and was heated under reflux for 16h with stirring. The off-white microcrystalline solid was collected by filtration, washed with water and dried in air. The empirical formula for the complex, as determined by thermogravimetric analysis, was; $Zn[SCH_2CH(NH_2)CO_2]$. This empirical formula was confirmed by matching the Fourier transform infra-red spectrum for the product with a reference spectrum for this complex, Shindo and Brown, J.Am.Chem.Soc. 87 (1965) 1904–1909.

2. Size Reduction of Zinc Cysteinate 2.1 Sonication

Zinc cysteinate suspensions in distilled water (1%w/v) were sonicated over ice for 5 minutes with a ultrasonic probe at maximum amplitude(Soniprep, MSE, U.K.).

2.2 Laser Light Scattering

Aliquots of sonicated suspension were placed in a Malvern Mastersizer. A 300 mm lens with a 3 mm path length cell was connected to the small sample presentation unit which was stirred continuously. Light scattering data was analysed using a sample presentation code of 0700.

Cumulative mass distributions were prepared using a computer spreadsheet program (Microsoft Excell®). The particle size data quoted, however, were obtained directly from the Mastersizer output.

3. Skin Deposition Studies 3.1 Preparation of Formulations

In order to calculate the equivalent amount of free cysteine for a given amount of complexed material the following empirical formula for the zinc cysteinate complex was used; $Zn[SCH_2CH(NH_2)CO_2]$, i.e. cysteine makes up 64.96% of the total formula weight.

Differences in the detection methods used for the free and the complexed cysteine meant that, formulations containing free cysteine included radiolabelled cysteine, and formulations containing complexed cysteine did not contain any radiolabel.

Two types of shampoo were prepared for both the free and the conplexed cysteine. One shampoo with a deposition aid, JAGUAR, and one without. The shampos had the following formulations:

| | % w/w ingredient | | | |
|---|---|---|---|---|
| | free cysteine formulations | | complexed cysteine formulations | |
| | with deposition aid | without deposition aid | with deposition aid | without deposition aid |
| cysteine | 1.39 | 1.38 | | |
| 'cysteine equivalent' | | | 1.38 | 1.38 |
| deposition aid: JAGUAR C13S (guar hydroxypropyl trimonium chloride) | 0.10 | — | 0.10 | — |

-continued

| | % w/w ingredient | | | |
|---|---|---|---|---|
| | free cysteine formulations | | complexed cysteine formulations | |
| | with deposition aid | without deposition aid | with deposition aid | without deposition aid |
| sodium laureth sulphate | 14.00 | 14.00 | 14.00 | 14.00 |
| cocamidopropyl betaine | 2.00 | 2.00 | 2.00 | 2.00 |
| dimethiconol and TEA-dodecyl-benzene sulphonate | 1.60 | 1.60 | 1.60 | 1.60 |
| sodium benzoate | 0.50 | 0.50 | 0.50 | 0.50 |
| Amplitude 484 | 0.50 | 0.50 | 0.50 | 0.50 |
| glycol distearate (and) laureth-4 (and) cocamidopropyl betaine | 8.00 | 8.00 | 8.00 | 8.00 |
| sodium chloride | 1.00 | 1.00 | 1.00 | 1.00 |
| citric acid | to pH 4.5–5.0 | to pH 4.5–5.0 | to pH 4.5–5.0 | to pH 4.5–5.0 |
| water | to 100 | to 100 | to 100 | to 100 |

In order to mimic in-use conditions as closely as possible, each shampoo was diluted tenfold with water prior to application to the skin. This tenfold dilution reflects the dilution that occurs when people apply shampoo to wet hair.

For each free cysteine formulation, 45.4 μl of L-[$^{35}$S]-cysteine (480 μCi on the day of preparation), 30 μl of shampoo and 224.6 μl of 0.185%w/v L-cysteine were mixed together in a plastic microcentrifuge tube. This produced 300 μl of 1 in 10 diluted shampoo suitable for dosing over 10 diffusion cells; each dose containing 40 μCi L-[$^{35}$S]-cysteine, having a volume of 25 μl and a cysteine concentration of 138%w/w.

For each complexed cysteine formulation, 1ml of shampoo was mixed with 2.12 ml of 0.212%w/v sonicated zinc cysteinate suspension and 6.88 ml of water. This produced 10 ml of 1 in 10 diluted shampoo with an equivalent cysteine concentration of 1.38%w/w. The zinc cysteinate suspension was prepared using the ultrasonic probe method detailed in 2.1 above. The particle size of the size-reduced zinc cysteinate was checked using Laser Light Scattering (2.2 above). The mass median diameter of the size-reduced zinc cysteinate was determined to be 8.27 μm. The particle size distribution was unimodal; 10% of the particles being <2.91 μm in diameter and 90% <22.46 μm.

3.2 Preparation of the Skin

The skin of the back of a two-month-old pig was used. First the skin was washed with 75% ethanol. This was done in order to remove sebum. Then the hairs were clipped off with an electric clipper (Oster, U.S.A.). Subcutaneous fat was scraped away with a post mortem knife (Raymond and Lamb). The prepared skin was then stored frozen until use. On the day of the experiment, the skin was thawed, dermatomed to a thickness of approx. 500 μm (Deca Dermatome, DePuy Healthcare, Leeds, U.K.) and then floated on Dubecco's modified phosphate buffered saline (pH7.4 containing 0.1% glucose, DMPBS).4

3.3 Skin Deposition Experiments

Diffusion experiments used Teflon® flow-through diffusion cells, (Crown Bioscientific Inc, Somerville, N.J., U.S.A.). The cells had a receptor volume of 130 μl and an exposed surface area of 0.38 cm$^2$. Cells were maintained at a temperature of 37° C. on metal aluminium heating blocks (Posiblock® Diffusion Cell Heater, Crown Glass Co.) heated by a circulating water bath. In this way the skin surface temperature was held at approximately 32° C.; normal skin surface temperature. Receptor compartments were filled with DMPBS to maintain good skin hydration.

For each of the four formulations, 25 μl of 1 in 10 diluted formulation was applied to the skin. The dose volume used was chosen on the basis that usually 5 g of product is applied to a typical scalp surface-area of 700 cm$^2$, and therefore that the undiluted shampoo dose per unit area is 7.1 mg/cm$^2$, and therefore that the dose per 0.38 cm$^2$ is approximately 2.7 μl. This equates to approximately 25 μl of 1 in 10 diluted product.

Dosing was performed with a 25 μl positive displacement pipette (Anachem, Luton, U.K.). Formulations were applied for 1 minute and rinsed off with 10×0.5 ml of DMPBS. The buffer was applied to the skin using a 1 ml Gilson pipette and taken off with a disposable pipette. The skin surface was rinsed three times with each wash by aspirating and reapplying the buffer.

After washing, the skin was left in the diffusion cells for 2 hours. Skin samples were then taken out of each cell and the application area cut from the trimmings with a pair of scissors. In radiolabel experiments, skin samples were solubilised in 2 ml of 90%v/v Soluene-350® in distilled water. Samples were solubilised overnight at 50° C. Solubilised samples were mixed with 16 ml Hionic-Fluor® (Packard Instrument Co.) prior to scintillation counting.

In radiolabel experiments, all samples were counted on a Beckman LS6000IC liquid scintillation counter (Beckman Instruments, Inc., Fullerton, Calif., U.S.A.).

3.4 Atomic Absorption Spectroscopy

Blank and treated skin samples (typically 10–20 mg.) were weighed into screw-top PTFE liners and 0.25 ml of concentrated nitric acid added. The liner was capped, placed inside a stainless steel digestion vessel and heated at 140° C. for 2 hours. After cooling the digests were diluted to 10 ml. with deionised water.

Tissue digests were analysed by comparison against known standards using flame atomic absorption spectrometry under the following conditions: air/acetylene flame, wavelength=213 nm, slit width=0.7 nm.

Results

A summary of skin deposition data is shown below in Table 1. Values represent means of 8–10 replicates. Values in brackets represent 2× standard error.

TABLE 1

| | % dose deposited | |
|---|---|---|
| | without JAGUAR | with JAGUAR |
| free cysteine | 0.51 (0.26) | 0.83 (0.31) |
| zinc cysteinate | 1.81 (0.98) | 4.85 (1.81) |

Conclusions

Statistical analysis revealed that for both zinc cysteinate treatments, zinc levels in the skin samples as measured by atomic absorption spectroscopy were significantly greater than blank skin values ($P<0.05$, Student's T-test, equal variances). Furthermore, zinc cysteinate deposition was significantly improved by inclusion of the Jaguar deposition aid ($P<0.05$, Student's T-test, equal variances). As expected, Jaguar had no effect on the deposition of the free cysteine ($P<0.05$, Student's T-test, equal variances).

What is claimed is:

1. A rinse-off hair treatment composition for improved delivery of amino-acid to the hair and/or scalp comprising:

(a) a particulate metal-amino acid complex;

(b) at least one surfactant; and (c) a polymeric, water-soluble deposition aid.

2. A composition according to claim 1, in which the metal ion has a valency of at least 2.

3. A composition according to claim 1 or 2, in which the amino acid is selected from the group consisting of cysteine, arginine, serine, glutamic acid, glutamine, isoleucine, lysine, methionine valine, and mixtures thereof.

4. A composition according to any of claims 1 to 3 in which the particulate metal-amino acid complex is zinc cysteinate or zinc glutamate, or a mixture of the two.

5. A composition according to any preceding claim, in which the average particle size of the particulate metal amino-acid complex is from 3–10 microns.

6. A composition according to any preceding claim which is a shampoo composition comprising from 0.5 to 30% by weight of a deterging surfactant selected from anionic, nonionic, amphoteric and zwitterionic surfactants, and mixtures thereof.

7. A composition according to any preceding claim in which the deposition aid is selected from the group consisting of cationic polyacrylamides, and cationic guar derivatives.

8. A method of enhancing the deposition of an amino acid from a rinse-off hair treatment composition, to the hair comprising incorporating the amino acid into the composition in the form of a particulate metal-amino acid complex.

9. A composition in accordance with claim 1, wherein said deposition aid is to enhance deposition of particles of said metal-amino acid complex on the hair and wherein said deposition aid is a homopolymer with a molecular weight between 5,000 and 10,000,000, and wherein said homopolymer has cationic nitrogen containing groups, and wherein the cationic charge density of the deposition aid is at least 0.1 milli-equivalents per gram to 4 milli-equivalents per gram.

10. A composition according to claim 1, wherein said deposition aid is a copolymer containing spacer non-cationic monomer units and said copolymer is of vinyl monomers selected from the group consisting of acrylamide, methacrylamide, alkyl and dialkyl acrylamides, alkyl and dialkyl methacrylamides, alkyl acrylates, alkyl methacrylates, vinyl caprolactone and vinyl pyrrolidine.

11. A deposition aid in accordance with claim 9, wherein said cationic amines can be primary, secondary or tertiary amines.

12. A composition according to claim 1, wherein said deposition aid is guar hydroxypropyltrimonium chloride.

* * * * *